United States Patent [19]

Kuypers et al.

[11] Patent Number: 5,577,494
[45] Date of Patent: Nov. 26, 1996

[54] SUPERABSORBENT FIBER COMPOSITIONS DEMONSTRATING EFFICIENT RETENTION OF EXHALED HEAT AND MOISTURE

[75] Inventors: Maurice H. Kuypers, Oakdale; Corazon C. Brizuela, Woodbury; Lawrence W. Craighead, Mendota Heights; David P. Swanson, Woodbury, all of Minn.

[73] Assignee: Minnesota Mining and Manufacturing Company, St. Paul, Minn.

[21] Appl. No.: 288,874

[22] Filed: Aug. 10, 1994

Related U.S. Application Data

[63] Continuation of Ser. No. 944,394, Sep. 14, 1992, abandoned.

[51] Int. Cl.$^6$ ..................................................... A62B 18/08
[52] U.S. Cl. ........................... 128/201.13; 128/204.13; 128/204.17; 128/205.12
[58] Field of Search ................... 128/201.13, 204.13, 128/204.17, 205.12, 205.19

[56] References Cited

U.S. PATENT DOCUMENTS

| | | | |
|---|---|---|---|
| 3,102,537 | 9/1963 | Bartlett, Jr. | 128/142 |
| 3,881,482 | 5/1975 | Lindholm | 128/212 |
| 3,895,675 | 7/1975 | Rein et al. | 165/164 |
| 4,090,513 | 5/1978 | Togawa | 128/212 |
| 4,327,717 | 5/1982 | Oetjen et al. | 128/201.13 |
| 4,516,573 | 5/1985 | Gedeon | 128/201.13 |
| 4,609,584 | 9/1986 | Cutler et al. | 428/156 |
| 4,771,770 | 9/1988 | Artemenko et al. | 128/201.13 |
| 4,874,659 | 10/1989 | Ando et al. | 128/205.29 |
| 4,963,638 | 10/1990 | Pazos et al. | 528/65 |
| 5,002,814 | 3/1991 | Knack et al. | 428/85 |
| 5,022,394 | 6/1991 | Chmielinski | 128/207.14 |
| 5,035,236 | 7/1991 | Kanegaonkar | 128/201.13 |
| 5,042,468 | 8/1991 | Lambert | 128/200.26 |

FOREIGN PATENT DOCUMENTS

| | | | |
|---|---|---|---|
| 1259869 | 6/1986 | Canada | A61M 16/00 |
| 0265163 | 4/1988 | European Pat. Off. . | |
| 0269462 | 6/1988 | European Pat. Off. . | |
| 0391814 | 10/1990 | European Pat. Off. | D01D 5/253 |
| 0409402 | 1/1991 | European Pat. Off. | A61M 16/00 |
| 01-104829 | 10/1987 | Japan . | |
| 2216208 | 2/1989 | Japan . | |
| WO90/12130 | 10/1990 | WIPO | D01D 5/253 |
| WO93/16749 | 9/1993 | WIPO . | |

*Primary Examiner*—Aaron J. Lewis
*Attorney, Agent, or Firm*—Gary L. Griswold; Walter N. Kirn; William J. Bond

[57] ABSTRACT

A heat and moisture exchange media and device is provided from structural matrix fibers and superabsorbent fibers.

12 Claims, 1 Drawing Sheet

SUPERABSORBENT FIBER COMPOSITIONS DEMONSTRATING EFFICIENT RETENTION OF EXHALED HEAT AND MOISTURE This is a continuation of application Ser. No. 07/944,394 filed Sep. 14, 1992, now abandoned.

BACKGROUND AND FIELD OF THE INVENTION

The invention described concerns a heat and moisture exchange media and particularly an improved fibrous media in the form of a nonwoven web.

A number of different approaches to heat and moisture exchange media, media arrangement, and housing designs have been proposed in the art. For example, U.S. Pat. No. 4,090,513 (Togawa) proposes a heat/moisture exchange device for attachment to a cannula inserted into the trachea. The heat/moisture exchange media comprises alternating layers of heat-conductive sheets (aluminum mesh) and heat-insulating sheets (gauze or a nonwoven fabric). It is stressed that the sheets should be perpendicular to the passage of air to create air layers isolating the heat-insulating layers to sharpen the temperature gradient across the body. A disadvantage with this media and the media arrangement design is the increase in the mass of the media and its resulting dead space.

Another alternating layer media is described in U.S. Pat. No. 4,771,770 (Artemenko et al.), directed to a heat/moisture exchange device used in a regeneration-type breathing apparatus. The heat/moisture exchange material comprises alternating layers of a nonwoven hydrophilic material impregnated, with a hygroscopic substance, with adjacent lower-density hydrophobic webs. Air distribution means are provided on either face of the body to direct more air to the peripheral edges of the medium. This device is bulky and the hygroscopic materials described are water soluble, which can be ingested by returned condensed water vapor.

Other patents also describe the use of media impregnated with water soluble hygroscopic material. Canadian Patent No. 1 259 869 describes a heat/moisture exchange medium comprised of a corrugated paper product impregnated with a hygroscopic material such as lithium chloride, glycols, or potassium chloride or acrylic acid, glycerin (used in antifreeze, a carcinogen) being most preferred. The corrugations are stacked, as opposed to a roll form, stated as providing a more non-uniform pressure drop and fluid flow, referring to several prior Japanese applications (see also U.S. Pat. No. 5,022,394). U.S. Pat. No. 5,042,468 (Lambert) describes a specific breathing device using a heat/moisture exchange medium comprising spirally-wound strips of corrugated cardboard impregnated with hygroscopic material or other conventional media. U.S. Pat. No. 4,516,573 (Gedeon) describes a heat/moisture exchange device, the media comprising polypropylene nonwovens impregnated with conventional hygroscopic substances. Problems again can arise due to the water solubility of the hygroscopic material, which can be subsequently returned to the patient. The water-soluble hygroscopic material also requires impregnation of the carrier which can complicate manufacturability.

EPA No. 265,163 describes a heat/moisture exchange device for attachment to tracheal or tracheostomy tubes. The material disclosed contains a layer of electrostatically charged polypropylene and a second layer of a pre-treated hydrophilic open-cell polyurethane foam able to absorb approximately 30 times its weight in moisture. Both layers act to condense moisture. U.S. Pat. No. 3,881,482 (Lindholm) describes a heat/moisture exchange device, the media comprising a soft open-celled plastic such as polyurethane or polyethylene foam. These foam layers would generally exhibit excessive pressure drops.

U.S. Pat. No. 5,035,236 (Kanegaonkar) describes a device comprising a corrugated material of glass fiber; the glass fiber media is transverse to the direction of air flow. The primary purpose of this media appears to be as a filter although the patent also notes that it has some heat/moisture exchange capabilities.

U.S. Pat. No. 4,327,717 (Oetjen et al.) describes an unusual heat/moisture exchange device where the heat/moisture exchange is conducted in parallel, hollow fibers of a permeable diaphragm material coated on one surface with copper or silver by cathode sputtering. This approach would be exceedingly costly and difficult to manufacture.

BRIEF SUMMARY OF THE INVENTION

A heat and moisture exchange media is proposed in the form of a fibrous nonwoven material. The fibers of the nonwoven comprise an interengaging network of matrix fibers and contained superabsorbent fibers. The superabsorbent fibers are preferably used in amounts from about 5 to 50 percent of the nonwoven fibers. The interengaging matrix fibers can be unconsolidated or consolidated by mechanical or nonmechanical mechanisms, including the use of bonding matrix fibers and/or heat treatment. Matrix fibers having external capillary fluid wicking channels provide superior performance over a broad tidal volume spectrum. The nonwoven media is easy to manufacture directly without the need for post formulation impregnation treatments and provides excellent heat and moisture exchange performance without the potential for dissolving of the absorbent media and possible return of water-soluble hygroscopic material to the patient by condensed moisture.

DETAILED DESCRIPTION OF THE INVENTION

Figure 1:
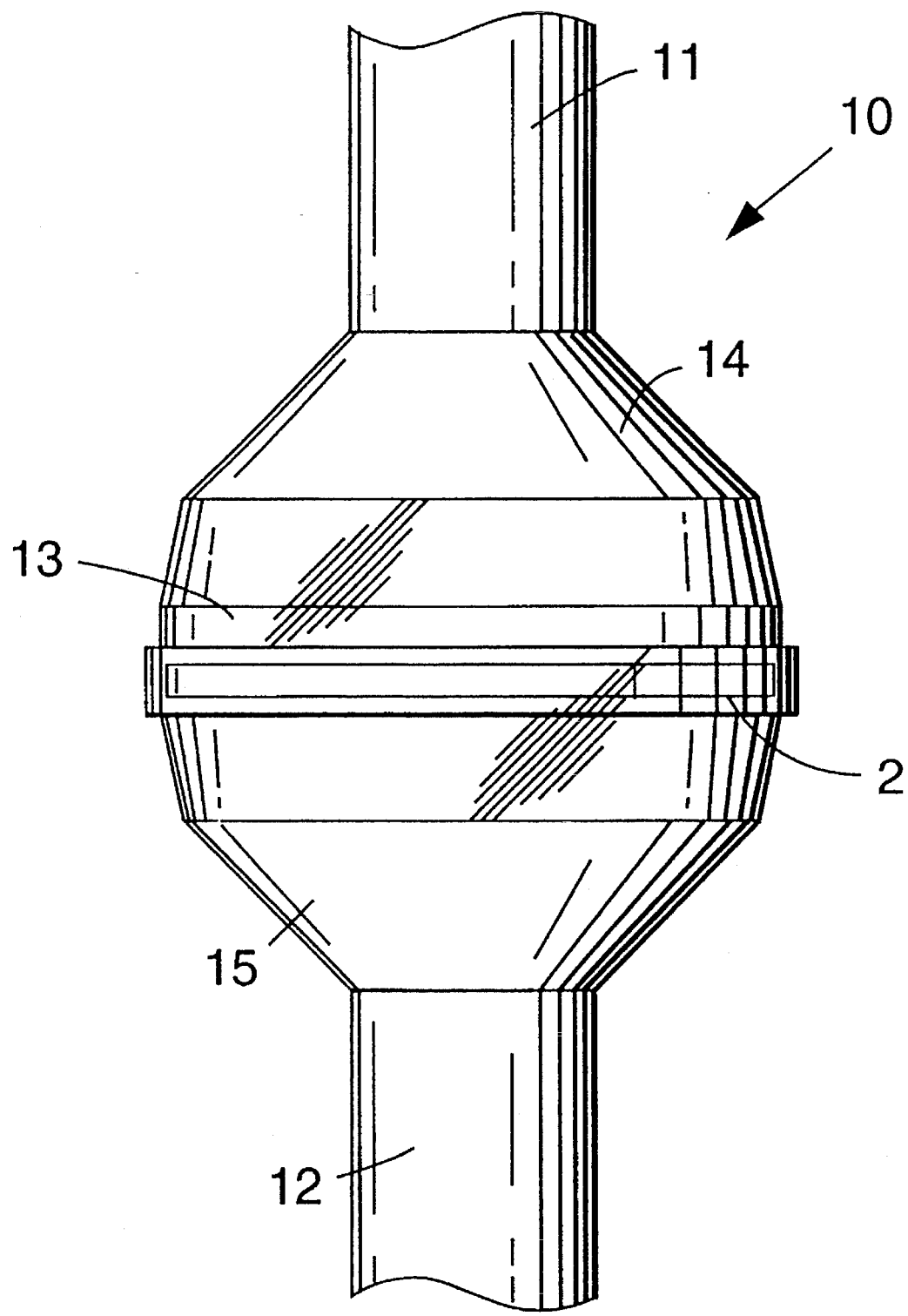
FIG. 1 is a conventional heat and moisture exchange device using the invention nonwoven heat and moisture exchange media.

The invention heat/moisture exchange media could be employed in a heat and moisture exchange device housing 10 such as that generally represented by FIG. 1, however, any suitable housing can be used. An inlet at one end port, 11 or 12, of the exchange housing would be connected to a conduit such as a tube (not shown) by conventional means, which tube would then be in fluid communication with the trachea of a patient. At the opposite end outlet port, 11 or 12, of the exchanger 10 would be connected to a second conduit such as a branched tube where the two other ends of the branched tube would be connected to a breathing apparatus, e.g., a ventilation device. In a ventilation device, inhalation air would pass down one leg of the branched tube then successively through the exchanger 10, the first tube and into the patient. Exhalation air would successively pass out through the first tube, the exchanger 10 and through the other leg of the branched tube. Although this is a conventional arrangement for use of the invention heat/moisture exchange media, the media can be used in other breathing apparatus where heat and moisture exchange is required, such as in rebreathing devices.

The exchange housing 10 axial inlet and exit ports 11 and 12 are of a smaller diameter than the central portion 13 adapted to hold the media 2. The inlet and outlet ports 11 and 12 and the central portion 13 are connected by funnel transition regions 14 and 15, which may have an angle of from about 90° to about 10° from the housing flow axis. A short highly tapered transition zone is generally preferred. However, housing designs can be used without transition regions by appropriate use of baffles and/or a tangential inlet port and/or outlet port as is known in the art. The housing can be unitary or be formed of interlocking halves to allow for replacement of the media 2. The interior of the housing 12 is generally hollow, but can include various forms of flow diverters, baffles or flow disruption means to more evenly distribute air flow to the media or provide for turbulent flow.

The inlet port and outlet port will generally have a cross sectional flow area substantially smaller than the largest cross sectional flow area of the central portion 13 so as to minimize the amount of dead space in the breathing apparatus system, the dead space comprises the housing 12 and connecting conduits to the patient and the source of breathable air, e.g., the atmosphere or the exit of a regeneration device.

The invention heat/moisture exchange media comprises a coherent admixture of structural interengaging matrix fibers, contained superabsorbent material, and optionally a binding fiber, which may also function as a matrix fiber. The media is generally in the form of a fibrous nonwoven web comprised of the matrix fibers, superabsorbent fibers and other optional fibers or fillers.

The structural matrix fibers are preferably hydrophilic fibers, although hydrophobic fibers can also be employed. These structural matrix fibers provide a nonwoven web of interengaging fibers with an open pore structure. Examples of suitable hydrophilic matrix fibers include cellulose fibers, rayon fibers, polyester fibers, hydrophilized hydrophobic fibers, such as surfactant-coated or -treated fibers, or silica-treated hydrophobic thermoplastic fibers (e.g., polyolefins or polyamide fibers). A single matrix fiber or combinations of matrix fibers along with the other fibers comprising the nonwoven web combine to form the invention nonwoven web heat and moisture exchange media.

The superabsorbent material is preferably comprised of superabsorbent fibers which are admixed with the interengaging matrix fibers of the nonwoven web. Any conventional superabsorbent fiber of sufficient length, e.g., greater than 5 mm, preferably greater than 25 mm, is generally suitable, such as synthetic superabsorbent fibers of the sheath/core, island-in-sea, or side-by-side multi-component construction. These conventional synthetic superabsorbent fibers would include treated polyacrylonitrile fibers (e.g., treated with metal hydroxides or ammonia), crosslinked partially neutralized maleic anhydride copolymer spun fibers, polyacrylonitriles co-spun with superabsorbent polymers such as acrylate/acrylonitrile copolymers, crosslinked polyacrylate, and copolymer fibers, such as described in Japanese Patent No. 89/104,829, fiber flocks containing superabsorbent as described in U.S. Pat. No. 5,002,814, or polyoxyalkylene glycol fibers such as described by U.S. Pat. No. 4,963,638. Natural-based superabsorbent fibers such as crosslinked polysaccharides or modified cellulose products are also suitable. Cellulosic-based superabsorbents are formed generally by esterification, etherification or grafting of cellulose fibers, the esters commonly being formed by heat-treating of ether precursors. These superabsorbent fibers can then be formed into suitable length macro-fibers by wet or dry spinning, by extruding into solvent exchange baths or in dry air. Viscose solution spinning with viscose blend to produce a superabsorbent rayon is also possible. Preferred are the synthetic fiber superabsorbents such as Toyobo Lanseal™ or N-38, Allied Colloid FSA type 102 or Arco Fibersorb™. Generally, a superabsorbent fiber will absorb at least 10 times its weight in water, preferably at least 30 times its weight.

The media also preferably incorporates bonding fibers as, or with, the interengaging matrix fibers. These bonding fibers can be formed of polymers having a melting point lower than the melting point(s) of the polymer(s) of the other matrix fibers or the superabsorbent fiber(s). Generally, the bonding matrix fiber polymer melting point is at least 20° C. below that of the next lowest melting point fiber (e.g., matrix or superabsorbent) or a matrix fiber layer of the bonding fiber. The bonding fiber can be a bicomponent fiber where one component is a fiber layer of the lower melting point bonding polymer and the other matrix layer(s) is a higher melting point matrix polymer. These bicomponent fibers are generally formed by a fiber spinning process. Examples include polyester/polyolefin bicomponent fibers where the polyolefin is a lower melting point polypropylene or polyethylene polymer or copolymer. Other low melting point polymers include ethylene/vinyl acetate copolymers or low melting point polyesters. The higher melting point components include polymers such as polyacrylonitrile, polyamides or higher melting point polyolefins. The use of these bonding fibers enables the web to be subject to a consolidating heat treatment to further increase the integrity of the fibrous matrix web without significant loss in web loft. This heat treatment can be accomplished under pressure, to produce higher density regions in the matrix or nonwoven web, or by a non-consolidating, (i.e., no pressure) heat treatment. Consolidation of the invention media is not generally limited, with the consolidation increasing the media surface area per unit volume. However, very small pore sizes in the nonwoven, resulting from high consolidation, are more easily blocked by water swelled superabsorbent fibers. Pore blocking increases pressure drop and decreases heat and moisture exchange efficiency.

Generally, the superabsorbent fiber polymers are used in amounts ranging from 5 to 80 percent of the media, and preferably 5 to 50 percent. The remaining fibers generally comprise matrix and/or bonding fibers. At fiber loading levels greater than 50 percent, the superabsorbent swelling fibers can cause micro distortions in the media porosity resulting in inefficient air flow distribution through the media and possible collapse of the web. At superabsorbent fiber loading levels below 5 percent of the media, the moisture exchange performance becomes excessively low.

When bonding fibers are employed, these typically are used in amounts ranging from 0 to 100 percent of the nonsuperabsorbent fibers preferably 20 to 80 percent. Bicomponent bonding fibers are preferred due to their superior ability to act as both matrix and bonding fibers.

In a particularly preferred embodiment, matrix fibers are employed which have longitudinal capillary fluid wicking channels or grooves on the exterior of the fibers, such fibers are described, for example, in European Patent Application No. 391 814 (claiming priority to U.S. patent application Ser. No. 333,651, filed Apr. 4, 1989). These wicking fibers would preferably have a hydrophilic surface coating or treatment. These shaped fibers provide superior performance for the invention media over an extended range of patient tidal volume applications. It is believed that the improvement in media performance is due to the ability of these fibers to rapidly wick condensed moisture uniformly throughout the matrix structure of the media, more uniformly utilizing the superabsorbent, while the channels also act as supplemental moisture reservoirs. As such, it is believed that the incoming dry air is exposed to a potentially larger and more uniform surface area of moisture-containing fibers without the disadvantageous effects of localized pore blocking caused by swelling or coalescing superabsorbent fibers. These capillary grooved fibers further help prevent the presence of excess moisture condensation on the interior of the housing. However, the occurrence of excessive housing condensation is noticeably reduced using the invention superabsorbent loaded nonwoven media even without the shaped fibers.

Further, the invention media preferably has no loose powders or soluble salts which can easily come free of the media as dust or dissolved salts and be absorbed or ingested by the patient.

In a preferred specific embodiment of the invention, the media comprises a web of matrix fibers and intermixed superabsorbent fibers in a nonwoven batt structure. The nonwoven batt structure can be directly incorporated into the exchange housing 10 as the exchange media 2. Advantageously, this nonwoven batt structure exchange media 2 can also have cover webs of bonded fibers, such as a spunbond polypropylene, to reduce the possibility of any fibers shedding from the batt and being inhaled by the patient. Also preferred is the use of a thin web of electrostatically charged fibers as a bacterial filter. A suitable electret filter is sold as Filtrete™ by 3M Corporation.

The invention media in a nonwoven web form can be consolidated by heat treating, needling, stitch bonding, or the like. Heat treatment consolidation coupled with a slight pressure is preferred when the web is used as a nonwoven batt. This treatment provides improved moisture exchange efficiency without adversely affecting pressure drop across the media. In a further alternative embodiment, the web material can be consolidated into a corrugated structure by passing a continuous web through a pair of co-rotating corrugating rolls (which may be heated), followed by bonding the corrugated medium onto a porous or non-porous backing material by use of adhesive point bonding, extrusion bonding, sonic welding or the like. The backing material can be formed of the invention medium consolidated into a film-like form, or strengthened nonwoven web material. The resulting corrugated structure can then be formed into a suitably shaped filter such as by spirally winding the corrugated material into a roll or by stacking parallel sheets of the corrugated material into a shape suitable for the housing. This corrugated construction has the advantage of significantly lowering pressure drop through the media due to the flow channels formed parallel to the air flow. This construction still offers significant surface area available for air contact with the heat/moisture exchange media of the invention.

The nonwoven media can be formed by any conventional wet lay or dry lay method, including carding, Rando™ web, or the like. The superabsorbent fibers could also be introduced into a fiber stream, such as a melt-blown fiber stream, and collected as a web. The melt-blown fibers and added staple fibers would function as matrix fibers.

The following examples are provided to illustrate presently contemplated preferred embodiments and the best mode for practicing the invention, but are not intended to be limiting thereof.

EXAMPLES 1–11

All the media was formed into a nonwoven web by hand or mechanical carding and placed in a standard housing such as shown in FIG. 1. The composition and basis weight for each of the filters are set forth in Table 1 below, in each of Examples 2–11 the media included a bacterial filter of a Filtrete™ web, which was tested alone in Example 1. The basis weight given for Examples 2–10 is that of a single layer of heat and moisture exchange media alone without the Filtrete™ web. These webs were produced on a carding machine. Examples 11–16 were produced by hand. For Examples 2–16, the total weight of HME media is reported in grams. For each of these examples, the media was arranged into a three-layer structure with the Filtrete™ filter layer between two layers of the media. For all media tested, the initial pressure drop was 5 mm $H_2O$ or less. The pressure drop decreased over time for the media containing the superabsorbent fibers.

TABLE 1

| Example | Basis Weight | Total Grams Media | Composition |
| --- | --- | --- | --- |
| Control | | | |
| C1 | 200 gm/m² | | 100% Filtrete ™ |
| 2 | 180 g/m² | 0.8 | 20% SA fiber[3], 30% shaped fiber[2], 50% binder fiber[1] |
| 3 | 360 g/m² | 1.2 | 20% SA fiber[3], 30% shaped fiber[2], 50% binder fiber[1] |
| 4 | 450 g/m² | 1.4 | 20% SA fiber[3], 30% shaped fiber[2], 50% binder fiber[1] |
| 5 | 450 g/m² | 1.4 | 20% SA fiber[3], 30% shaped fiber[2], 50% binder fiber[1] |
| 6 | 540 g/m² | 2.2 | 20% SA fiber[4], 40% shaped fiber[2], 40% binder fiber[5] |
| 7 | 540 g/m² | 2.2 | 20% SA fiber[4], 40% shaped fiber[2], 40% binder fiber[5] |
| 8 | 185 g/m² | 0.8 | 20% SA fiber[4], 40% shaped fiber[2], 40% binder fiber[5] |
| 9 | 185 g/m² | 0.8 | 20% SA fiber[4], 40% shaped fiber[2], 40% binder fiber[5] |
| 10 | 220 g/m² | 0.8 | 20% SA fiber[4], 40% shaped fiber[2], 40% binder fiber[5] |
| 11 | | 0.8 | 50% SA[3], 50% binder fiber[1] |
| 12 | | 0.8 | 50% SA fiber[3], 50% shaped fiber[2] |
| C13 | | 0.8 | 100% binder fiber[1] |
| C14 | | 0.8 | 100% shaped fiber[2] |
| 15 | | 0.8 | 5% SA fiber[3], 95% shaped fiber[2] |
| C16 | | 0.8 | 80% SA fiber[3], 20% shaped fiber[2] |

1. T255 bonding fiber available from Hoechst Celanese Corp., Charlotte, NC.
2. Wicking fiber available from Eastman Chemical Products, Kingsport, TN, prepared in accordance with PCT Application No. W090/12130.
3. Superabsorbent FSA fiber available from Allied Colloids, Inc., Suffolk, VA.
4. N38 superabsorbent available from Toyobo Co.
5. T 256 available from Hoeschst Celanese Corp., Charlotte, NC.

The examples with binder fibers were heated to a temperature of 375° F. (190° C.), and Examples 3, 4, 6 and 8 were additionally compressed under a roller from a thickness of about 3 cm to a thickness of 1 cm while still hot. The media of Examples 1–11 were then tested for moisture exchange efficacy with the results set forth in Table 2 below.

TABLE 2

| | Tidal Volume | | |
| --- | --- | --- | --- |
| Example | 250 cc | 500 cc | 1000 cc |
| Control | | 7.4 | |
| C1 | 12.9 | 8.4 | 6.1 |
| 2 | 20.0 | 19.3 | 19.3 |

TABLE 2-continued

| Example | Tidal Volume | | |
|---|---|---|---|
| | 250 cc | 500 cc | 1000 cc |
| 3 | 23.1 | 21.1 | 19.8 |
| 4 | | | 26.3 |
| 5 | | 25.1 | |
| 6 | | 30.1 | |
| 7 | | 31.5 | |
| 8 | | 25.9 | |
| 9 | | 22.2 | |
| 10 | 23.8 | 21.7 | 19.2 |
| 11 | | 19.8 | |
| 12 | | 23.3 | |
| C13 | | 13.1 | |
| C14 | | 13.0 | |
| 15 | | 16.9 | |
| C16 | | 22.3 | |

Table 2 shows that the use of superabsorbent fiber, coupled with the shaped fibers and binder fiber, provides good moisture exchange efficacy at a broad range of tidal volumes (note Examples 2, 3 & 10). The use of shaped fibers alone (Counterexample 14) does not appear distinguishable from binder fiber alone (Counterexample 13), however, the use of shaped fibers in conjunction with the superabsorbent fibers (Example 12) provides significantly improved performance over the combination of superabsorbent fiber and binder fiber (Example 11).

The use of a slightly compressed web (Examples 3, 4, 6 and 8) provided improved moisture exchange performance over uncompressed webs, however, surprisingly, the pressure drop for both versions was substantially identical at similar basis weights. Pressure drop for all invention webs was found to decrease or remain relatively constant over the test period. This is in contrast to conventional media which has a tendency to increase in pressure drop over the use period.

In Counterexample 16, the matrix fiber was not capable of maintaining the web shape in extended use, and the web collapsed as the superabsorbent fibers became wetted and swelled.

Control is the housing alone, which performed about the same as the use of Filtrete™ alone in Counterexample 1.

TEST METHODS

Moisture exchange efficiency

The media was tested according to draft International Standard ISO/DIS 9360 (1988). The results using this measurement method were generally significantly lower than results obtained by prior testing methodologies for all media. The media was tested for three (3) hours, with data collected on each hour. The results in Table 2 are averages of the hourly readings over the three-hour testing period. The performance generally became more stable over time. The moisture exchange efficiency in Table 2 is reported in mg/l.

We claim:

1. A heat and moisture exchange device comprising;

a housing means having a central portion, a first inlet means defining an inlet port, and a second outlet means defining an outlet port, said inlet port means adapted to be connected to a patient via a conduit means, and said outlet port means adapted to be connected to a breathing apparatus means, said control portion adapted to hold a heat and moisture exchange media, and a heat and moisture exchange media which will function as a heat and moisture exchange media comprising a coherent fiber admixture of structural inter-engaging matrix fibers and from 5 to 50 percent by weight included absorbent fibers, said absorbent fibers capable of absorbing at least 10 times their weight in water, said heat and moisture exchange media held in said central portion of said housing means wherein said absorbent fibers and matrix fiber admixture has a moisture exchange efficiency of at least 16.9 as determined according to ISO/DIS 9360-1988 at 500 cc volume.

2. The heat and moisture exchange device of claim 1 wherein said heat and moisture exchange media is in the form of a nonwoven web and said absorbent fibers are capable of absorbing at least 30 times their weight in water.

3. The heat and moisture exchange device of claim 2 wherein said structural matrix fibers comprise bonding fibers.

4. The heat and moisture exchange device of claim 3 wherein said bonding fibers comprise a bicomponent fiber comprised of a lower melting point bonding polymer and a higher melting point polymer.

5. The heat and moisture exchange device of claim 2 wherein said structural matrix fibers comprise shaped fibers.

6. The heat and moisture exchange device of claim 5 wherein said shaped fibers have channels or grooves on the exterior of said shaped fibers for wicking moisture.

7. The heat and moisture exchange device of claim 5 wherein said web further comprises bonding fibers.

8. The heat and moisture exchange device of claim 7 wherein said matrix fibers comprise shaped fibers having channels or grooves on the exterior of said shaped fibers wherein said bonding fibers comprise 20 to 80 percent of the nonabsorbent fibers.

9. The heat and moisture exchange device of claim 2 wherein said absorbent fibers have a length of at least 5 mm.

10. The heat and moisture exchange device of claim 2 further comprising a cover web at least on the face of said media facing the inlet port.

11. The heat and moisture exchange device of claim 2 wherein said heat and moisture exchange device further comprises a web of electrostatically charged fibers as a biological filter in said housing means.

12. The heat and moisture exchange device of claim 2 wherein the media is corrugated and arranged to provide flow passages in the direction of gas flow through the media.

* * * * *